United States Patent [19]

Kurkov

[11] 4,183,866
[45] Jan. 15, 1980

[54] METHOD FOR PREPARING 3-CYANOPROPANOL AND 2-PYRROLIDONE

[75] Inventor: Victor P. Kurkov, San Rafael, Calif.

[73] Assignee: Chevron Research Company, San Francisco, Calif.

[21] Appl. No.: 908,341

[22] Filed: May 22, 1978

[51] Int. Cl.$^2$ .................. C07C 120/00; C07C 121/34
[52] U.S. Cl. ...................... 260/465.6; 260/326.5 FN; 260/343.6
[58] Field of Search ..................... 260/465.6

[56] References Cited

U.S. PATENT DOCUMENTS

| | | | |
|---|---|---|---|
| 2,564,131 | 8/1951 | Schreyer | 260/465.6 X |
| 3,210,400 | 10/1965 | Brakebill | 260/465.6 X |
| 3,466,317 | 9/1969 | Kuper | 260/465.6 |

OTHER PUBLICATIONS

C.A., 60(1964), 11903h, Ajinomoto Co.
C.A., 58(1963), 4420f, Kato, et al.
C.A., 74(1971), 76048v, Wakamatsu, et al.
C.A., 71(1969), 87216n, Wakamatsu, et al.
C.A., 76(1972), 3341s, Sato, et al.
Nes, J. Org. Chem., 23, (1958), pp. 899–900.
Translation of Kogyo Kagaku Zasshi, 74(9), 1971, pp. 1830–1834 by Sato, et al.

*Primary Examiner*—Joseph Paul Brust
*Attorney, Agent, or Firm*—Dix A. Newell; T. G. DeJonghe; Lawrence S. Squires

[57] ABSTRACT

Processes for preparing 3-cyanopropanol and 2-pyrrolidone. The processes are characterized by the step of reacting 3-cyanopropanal with hydrogen in the presence of an especially prereduced copper-chromite catalyst to afford high yields of high-purity 3-cyanopropanol.

13 Claims, No Drawings

METHOD FOR PREPARING 3-CYANOPROPANOL AND 2-PYRROLIDONE

BACKGROUND OF THE INVENTION

1. Field of the Invention

This invention relates to processes for producing 3-cyanopropanol from 3-cyanopropanal. In a further aspect, the invention relates to processes for preparing 3-cyanopropanol comprising reacting 3-cyanopropanal with hydrogen in the presence of an especially prereduced copper-chromite catalyst. In a still further aspect the invention relates to processes for preparing 2-pyrrolidone comprising the step of reacting 3-cyanopropanal with hydrogen in the presence of the prereduced copper-chromite catalyst.

2. The Prior Art 3-cyanopropanol is an intermediate for the preparation of gamma-butyrolactone, a commercial solvent, and 2-pyrrolidone. 2-pyrrolidone can itself be used as a solvent or can be used as an intermediate for other commercial solvents. More importantly, however, 2-pyrrolidone can be homopolymerized to poly-2-pyrrolidone, commonly known as nylon-4. For example, one suitable polymerization process is described in U.S. Pat. No. 3,721,652.

Poly-2-pyrrolidone can be molded into fibers, films, and other shaped articles. Poly-2-pyrrolidone's advantages as a textile fiber having good water-retention properties are particularly notable.

In the preparation of poly-2-pyrrolidone it is very important to use very pure 2-pyrrolidone monomer, because the polymerization is very sensitive to impurities. Since the presence of certain impurities or by-products formed in the preparation of 2-pyrrolidone can inhibit the polymerization reaction or can, in fact, adversely accelerate the polymerization reaction, causing a poor-quality, low-molecular-weight polymer product to be produced. Thus, it is very important to prepare 2-pyrrolidone from high-purity intermediates to ensure than high-pyrity 2-pyrrolidone is obtained.

Accordingly, in one aspect, the present invention is concerned with an improved process for producing high yields of very high-quality 3-cyanopropanol reaction product mixture which can be used to prepare very pure 2-pyrrolidone.

The preparation of 3-cyanopropanol by the hydrogenation of 3-cyanopropanal is known and is disclosed in Kogyo Kagaku Zasshi, Vol. 74 (9), 1830–1834 (1971), using a cobalt carbonyl catalyst and in U.S. Pat. No. 3,141,895 using palladium-carbon, platinum-carbon, nickel or copper-chromium catalyst. The Kogyo publication also teaches that 3-cyanopropanol can be converted to pyrrolidone by heating with aqueous ammonia.

W. R. Ness teaches in the Journal of Organic Chemistry Vol. 23, pages 899 and 900 (1958) that boiling copper-chromium oxide in cyclohexanol increases the ability of this catalyst to hydrogenate acetone to 2-propanol at lower temperatures and to oxidize certain steroid alcohols to the corresponding ketones at lower temperatures. The JOC publication also teaches that during the activation treatment, the cyclohexanol is simultaneously oxidized to cyclohexanone.

It has now been discovered that with respect to the catalyzed reaction of 2-cyanopropanal with hydrogen that by treating a copper-chromite catalyst with hydrogen or an alkanol or cycloalkanol at elevated temperatures that not only is the activity of the catalyst increased, but surprisingly the selectivity of the catalyst for 2-cyanopropanol, and gamma-butyrolactone is greatly increased. The combination of increased activity (i.e., conversion) and increased selectivity is particularly surprising and affords a large compounded increase in the yields of the desired products, which can be readily converted to 2-pyrrolidone in high yields via treatment with ammonia.

SUMMARY OF THE INVENTION

In summary, one process of the invention comprises contacting 3-cyanopropanal with hydrogen in the presence of a copper-chromite catalyst which has been prereduced with hydrogen at elevated temperatures, to yield 3-cyanopropanol.

In summary, another process of the invention comprises contacting 3-cyanopropanal with hydrogen in the presence of a copper-chromite catalyst which has been prereduced with an alkanol or cycloalkanol at elevated temperatures, to yield 3-cyanopropanol.

In summary, the process of the invention for preparing 2-pyrrolidone comprises contacting 3-cyanopropanal with hydrogen in the presence of a copper-chromite catalyst which has been prereduced with hydrogen at elevated temperatures, to yield 3-cyanopropanol and gamma-butyrolactone and contacting the so-produced 3-cyanopropanol and gamma-butyrolactone with aqueous ammonia to convert said 3-cyanopropanol to 2-pyrrolidone.

In summary, the invention further comprises certain preferred reaction conditions and modes for effecting the aforementioned processes of the invention.

FURTHER DESCRIPTION OF THE INVENTION AND PREFERRED EMBODIMENTS

The process of the invention for preparing 3-cyanopropanol can be schematically represented by the following overall reaction equation. (Also, although a single reaction equation is represented, it should be appreciated that in actuality there are a number of competing reactions and by-products which could occur, and hence the need for a catalyst which is selective to 3-cyanopropanol, in accordance with the present invention).

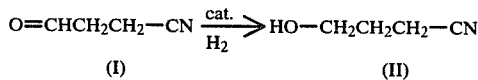

$$O=CHCH_2CH_2-CN \xrightarrow[H_2]{cat.} HO-CH_2CH_2CH_2-CN$$

(I)                   (II)

The process can be conveniently effected by contacting the desired compound of formula I with hydrogen in the presence of a copper-chromite catalyst which has been specifically prereduced as will be subsequently described hereinbelow.

The process is typically conducted at temperatures in the range from about 50° to 200° C., preferably from about 75° to 150° C., for from ½ to 6 hours, preferably about from ½ to 2 hours, and at hydrogen pressures of about from 1000 to 5000 psig of hydrogen. The reaction is conducted in the presence of a stoicheometric excess of hydrogen. Typically, a catalyst-to-compound ratio of formula I of about from 0.05 to 0.5 gram of catalyst per gram of compound I, and preferably about from 0.2 to 0.5 gram, is used. Best results are typically obtained using temperatures in the range about from 90° to 130°

C. for about from ½ to 2 hours using 2000 psig to 4000 psig of hydrogen.

Since the compounds of formula I are liquid under the reaction conditions, the process can be conducted either with or without a solvent. Conveniently, however, the process will be conducted using a solvent, since the conversion of the products of the present reaction to 2-pyrrolidone is typically conducted in a solvent and thus the solvent solution can be used directly without separation of the solvent. Suitable solvents which can be used include for example, water or suitable inert organic solvents, or aqueous mixtures thereof. Suitable inert organic solvents which can be used include, for example, benzene, toluene, alkanols, ethers, dioxane, tetrahydrofuran and the like and compatible mixtures thereof.

The resulting 3-cyanopropanol reaction product can also contain moderate quantities of gamma-butyrolactone and small amounts of 2-pyrrolidone. When the hydrogenation reaction is carried out in an aqueous solution, the resulting gamma-butyrolactone can be converted to 2-pyrrolidone via ammonolysis process similar to the process that converts 3-cyanopropanol to 2-pyrrolidone. Thus, although for convenience the process has been described as being selective to 3-cyanopropanol, it would be more accurate to say that the process is selective to 2-pyrrolidone precursors.

The reaction product can be separated and isolated by conventional procedures, such as filtration and distillation.

The starting materials of formula I are known compounds and can be prepared according to known procedures. For example, 3-cyanopropanal can be prepared by the procedure described in U.S. Pat. No. 2,978,481 by treating acrylonitrile with carbon monoxide and hydrogen in the presence of a cobalt carbonyl catalyst, preferably in a polar solvent such as methanol, ethanol, acetone, dioxane, etc. It is preferable to use good-quality 3-cyanopropanal in the present process. This is particularly important in the case where the starting material has been made by the conventional oxo process using a cobalt carbonyl catalyst because cobalt poisons the prereduced copper-chromite catalyst. The cobalt carbonyl catalyst can be removed from the aldehyde product reaction mixture by any suitable procedure; for example, by ion exchange or by heating the product mixture to precipitate metallic cobalt and then removing the precipitate by filtration, etc.

In a preferred mode, of the invention, the 3-cyanopropanal is prepared by in situ hydrolysis in water of a suitable acetal of 3-cyanopropanal. This mode is particularly convenient because 3-cyanopropanal is generally prepared from its acetals and as the water solution can be carried through the conversion of 3-cyanopropanol, or other 2-pyrrolidone precursors, to 2-pyrrolidone. Where this mode is used, the process is conducted in the same manner as described above, using water as the solvent, with the exception that 3-cyanopropanal acetal is initially used in place of 3-cyanopropanal and in situ hydrolyzed to 3-cyanopropanal. Also since the hydrolysis is an acid hydrolysis, it is preferred to add a small amount of acid (e.g., mineral acid or strong organic acid) to the water solvent. Suitable acetals which, for example, can be used can be represented by the following formula:

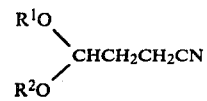

wherein $R^1$ and $R^2$ are independently selected from the group of lower alkyls having 1 through 6 carbon atoms.

The copper-chromite ($CuO \cdot CuCr_2O_4$) catalyst is prereduced by contacting the catalyst with hydrogen at elevated temperatures and preferably in the absence of oxygen. This can be conveniently effected by dispersing the catalyst in a suitable liquid carrier and then bubbling hydrogen through the liquid carrier or pressurizing the reaction vessel with hydrogen. Typically prereduction temperatures in the range of about 130° to 250° C. and preferably about from 150° to 200° C. and hydrogen pressures in the range of about from 100 to 5,000 psig are used. Suitable liquid carriers which can be used include, for example, alkanols, cycloalkanols, tetrahydrofuran, tetrahydropyran, gamma-butyrolactone, bis-2-ethoxyethyl/ether and the like and compatible mixtures thereof.

The prereduction can also be conveniently effected by simply contacting the catalyst with hydrogen at elevated temperatures (e.g., from about 130° to 250° C., preferably about from 150°–200° C., and elevated hydrogen pressures (e.g., 100 to 5000 psig). This mode of treatment is especially appropriate where a fixed-bed flow reactor is used for the 3-cyanopropanol process. Thus, the catalyst bed is treated by simply passing hydrogen through it at the elevated temperatures and hydrogen pressures, previously given.

The prereduction can also be conveniently effected by contacting the catalyst with an alcohol (e.g. alkanol or cycloalkanol) at elevated temperatures. In this instance, the copper-chromite oxidizes the alcohol to a carbonyl, and is concomitantly reduced, and also liberate hydrogen which can in turn further prereduce the catalyst. This treatment is also preferably conducted in the absence of air and hence typically is initially conducted under hydrogen or an inert atmosphere such as nitrogen. The treatment can be conveniently conducted by simply immersing the copper-chromite catalyst in the alcohol at elevated temperatures for a sufficient period of time to increase the selectivity and activity of the catalyst. Typically, temperatures in the range of 130° to 250° C., preferably about 150° to 200° C., are used and treatment times in the range of about 1 to 6 hours, preferably from 1 to 4 hours. Generally, lower treatment times can be used with higher temperatures and vice versa.

Suitable alkanols which can be used include, for example, methanol, ethanol, butanol, isopropanol, pentanol, hexanol, and the like and mixtures thereof. Suitable cycloalkanols which can be used include, for example, cyclopentanol, cyclohexanol, cycloheptanol, cyclodecanol and the like and mixtures thereof. Typically, alkanols having from 1 through 12 carbon atoms and cycloalkanols having from 5 through 12 carbon atoms are used. Higher alkanols and cycloalkanols can also be used, but generally are not as commercially convenient. Typically about from 3 to 20 grams of the alkanol or cycloalkanol is used per gram of the copper-chromite catalyst. Best results are typically obtained by conducting the treatment at temperatures in the range from about 140° to 170° C. for about 3 to 5 hours using cyclopentanol, cyclohexanol or 2-hexanol as the alcohol.

Considering now the overall process of the invention for preparing 2-pyrrolidone from 3-cyanopropanal. In the first step of this process, 3-cyanopropanal is treated as described above to yield 2-pyrrolidone precursors (e.g., 3-cyanopropanol, etc.) reaction product. This reaction product is then treated with ammonia, causing a shift in chemical equilibrium and yielding 2-pyrrolidone. Preferably, the copper-chromite catalyst is removed from the reaction product prior to the ammonia treatment, for example, by filtration. The ammonia treatment can be conducted in a suitable organic solvent, but typically and conveniently is simply conducted using aqueous ammonium hydroxide. Typically, the treatment is conducted at temperatures in the range of about 150° to 300° C. and preferably from about 180° to 230° C. for about from 1 to 6 hours, and preferably from about 2 to 4 hours. As before noted, the ammonia is not consumed in the reaction, but merely serves to shift the reaction equilibrium to 2-pyrrolidone as between 2-pyrrolidone and gamma-butyrolactone. Typically, mol ratios of ammonia to 2-pyrrolidone precursor (e.g., 3-cyanopropanol) in the range of about from 1 to 20, preferably about from 5 to 15 mols of ammonia per mol of 2-pyrrolidone precursor is used. Typically, mol ratios of water to 3-cyanopropanol and/or gamma-butyrolactone in the range of about from 2 to 20, preferably about from 4 to 15 mol of water per mol of 3-cyanopropanol and/or gamma-butyrolactone are used. The mol ratio of water is not critical, so long as stoichiometric or greater amounts are used and thus amounts of water substantially above this range could also be used, though generally this merely renders recovery of the 2-pyrrolidone product more difficult.

The resulting 2-pyrrolidone can be recovered from the reaction mixture by any suitable procedure such as, for example, distillation or extraction, etc. As before noted, the resulting 2-pyrrolidone is a very-high-purity product which can be advantageously polymerized to poly-2-pyrrolidone by any suitable procedure.

The process of the present invention can be conducted as a batch, semi-continuous or continuous process using the appropriate reactor (e.g., stirred-reactors, fixed-catalyst bed reactor, etc.).

Also, where typical reaction or process conditions have been given, it should be appreciated that conditions both above and below these ranges could also be used, though typically with poorer results or economics.

Definitions

As used herein, the following terms have the following meanings unless expressly stated to the contrary.

The term "alkyl" refers to branched or straight chain alkyl groups having 1 through 15 carbon atoms.

The term "lower alkyl" refers to such alkyl groups having 1 through 6 carbon atoms.

The term "alkanol" refers to groups having the formula R'OH wherein R' is a branched-chain or straight-chain alkyl group having from one through 15 carbon atoms. The term "cycloalkanol" refers to cycloalkanols having from 3 through 15 ring carbon atoms.

The term "pyrrolidone" refers to 2-pyrrolidone.

A further understanding of the invention can be had from the following non-limiting examples.

EXAMPLE 1

This example illustrates a method of prereducing the copper-chromite catalyst by treatment with an alcohol. In this example, 18 grams of copper chromite was added to 150 ml of cyclohexanol and then heated at 160° C., under a nitrogen atmosphere, for 4 hours. The catalyst was then recovered by filtration and then washed with acetone and dried.

EXAMPLE 2

This example illustrates the prereducing of the copper-chromite catalyst by treatment with hydrogen in an organic liquid medium. In this example, 2 g of copper chromite was added to 50 ml of methanol; the reaction vessel was flushed with hydrogen, and then pressurized to 2800 psig with hydrogen and heated for 1 hour at 160° C. The catalyst was used in situ for hydrogenation of 3-cyanopropanal (Example 4).

EXAMPLE 3

This example illustrates the prereducing of the copper-chromite catalyst by reduction with hydrogen in an organic liquid medium. In this example, 2 g of copper chromite was added to 25 ml of gamma-butyrolactone; the reaction vessel was flushed with hydrogen, and then pressurized to 2800 psig with hydrogen and heated for 1 hour at 160° C. The catalyst was used in situ for hydrogenation of 3-cyanopropanol (Example 5).

EXAMPLE 4

This example illustrates the process of the invention using the prereduced catalyst vs. the same process using the untreated catalyst.

In this example, 0.05 mol of 3-cyanopropanal (the 3-cyanopropanal was prepared in situ by acid catalyzed hydrolysis of 3-cyanopropanal dimethyl acetal), 2 grams of catalyst, 6 grams of ethoxyethanol and sufficient water to give the mixture a volume of 50 mililiters was placed in a reaction vessel. The vessel was pressurized to 2800 psig of hydrogen and then heated at the temperature indicated hereinbelow in Table I for five hours (The ethoxyethanol was merely added as a chromatography standard and does not affect the reaction.) Samples were taken and analyzed at the end of the reaction times indicated in the table. The experiment was repeated four times, once using copper chromite, which had not been prereduced and twice using copper chromite which had been prereduced in accordance with the procedure of Example 1, hereinabove, and once using copper-chromite catalyst which had been prereduced in accordance with the procedure of Example 2 hereinabove.

The results of these tests are summarized in the following Table I.

TABLE I

| Pre-reduction Procedure | Reaction Temperatures °C. | Reaction Time/Hours | Conv. % *1 | Selectivity Percent *2 |
|---|---|---|---|---|
| None | 100 | 1 | 46 | Trace |
|  |  | 5 | 100 | 8.5 |
| Example 1 | 98 | 1 | 66 | 74.7 |
|  |  | 5 | 100 | 90.6 |
| Example 1 | 100 | 1 | 62.3 | 57.6 |
|  |  | 5 | 100 | 91.2 |
| Example 2 | 100 | 1 | 70.8 | 94.3 |

TABLE I-continued

| Prereduction Procedure | Reaction Temperatures °C. | Reaction Time/Hours | Conv. % *1 | Selectivity Percent *2 |
|---|---|---|---|---|
| | | 2 | 100 | 93.3 |

*1 Conversion Percent is defined as $\frac{\text{3-cyanopropanal reacted}}{\text{charged}} \times 100$

*2 Selectivity Percent is defined as $\frac{\text{3-cyanopropanol}}{\text{3-cyanopropanol reacted}} \times 100$ The copper-chromite catalyst used in all of the above experiments was a powdered catalyst having a surface area of about 20–30 m²/g, containing 47% wt. CuO and 47% wt. CrO₃ and the remainder inert diluent, and is sold under the trade name CALSICAT 104, by the Mallinckrodt Company Calsicat Division.

As can be seen from the above table, after 1 hour of operation, the process of the present invention using the prereduced catalyst afforded much better conversions and selectivities than did the process using the unprereduced catalyst. More importantly, however, at the end of five hours or complete conversion, the process using the prereduced catalyst afforded a selectivity to 2-pyrrolidone precursors (i.e., 3-cyanopropanol, gamma-butyrolactone or 2-pyrrolidone) of only 8.5%, whereas in each case the process of the present invention afforded a selectivity of at least 90%. The combination of increased conversion and selectivity resulted in greatly improved yields of the desired products.

EXAMPLE 5

This example further illustrates the process of the present invention using the prereduced catalyst as compared with the identical process but using the unprereduced catalyst. In this example, a mixture containing 0.05 mol of 3-cyanopropanal, 2 grams of catalyst, and 6 grams of ethoxypropanol and sufficient gamma-butyrolactone to make a total volume of 50 ml was pressurized with hydrogen to a pressure of 2800 psig and heated at 160° C. for the period of time indicated in Table II hereinbelow. (The ethoxyethanol is merely a chromatography standard and does not affect the reaction.)

The example was repeated five times, once using the unprereduced copper-chromite catalyst and four times using catalysts which had been prereduced either in accordance with the procedure of Example 1 or the procedure of Example 3. Where the prereduced catalysts were used, the reaction was complete and discontinued after one hour. Where the unprereduced catalyst was used, the reaction was allowed to continue for five hours. The copper-chromite catalyst used in all of the trials in this example was a powdered catalyst having a surface area of about 30–70 m²/g and containing 47% wt. CuO and 47% wt. Cr₂O₃, and is sold under the trademark CALSICAT 105 by the Mallinckrodt Company, Calsicat Division. The results of these tests are summarized in the following Table II.

TABLE II

| Prereduction Procedure | Time, Hours | Conv., % *1 | Selectivity, % *2 |
|---|---|---|---|
| None | ½ | 12.5 | Trace |
| | 3 | 76.3 | 51.5 |
| | 5 | 99.0 | 64.9 |
| Example 1 | 1 | 100 | 97.3 |
| Example 1 | ½ | 91.6 | 100 |
| | 1 | 100 | 100 |
| Example 1 | ½ | 96.2 | 100 *3 |
| | 1 | 98.9 | 100 |
| Example 3 | ½ | 98.3 | 94.7 |
| | 1 | 100 | 98.2 |

*1 Conversion and selectivity are
*2 as defined in Table I hereinabove.
*3 In this run, ethyl acetate was used as the solvent in place of gamma-butyrolactone.

As can be seen from the above table, at the end of ½ hour at 160° C., the processes of the present invention, using the prereduced catalyst, showed much higher conversions and selectivities than did the process using the unprereduced catalyst, and at the end of one hour showed essentially complete conversions, whereas the unprereduced catalyst process showed only 76.3% conversion after 3 hours. More importantly, however, at the completion of the reaction, one hour in the case of the process of the present invention and five hours in the case of the process using the unprereduced catalyst, the selectivities of the processes using the prereduced catalyst were very substantially greater than the process using an unprereduced catalyst. Thus, the combined improvement in selectivity and conversion affords a substantial increase in the desired products.

Obviously, many modifications and variations of the invention, described hereinabove and below in the Claims, can be made without departing from the essence and scope thereof.

What is claimed is:

1. A process for preparing 3-cyanopropanol which comprises contacting a liquid reaction mixture comprising 3-cyanopropanal with a stoichiometric excess of hydrogen at temperatures in the range of about from 50 to 250° C. and hydrogen pressures in the range of about from 1,000 to 5,000 psig in the presence of a catalytically effective amount of a copper-chromite catalyst, which has been prereduced via contact with a reducing agent selected from the group consisting of hydrogen, alkanols, cycloalkanols or mixtures thereof at elevated temperatures to increase its selectivity, to yield said 3-cyanopropanol product.

2. The process of claim 1 wherein said liquid reaction mixture comprises water and wherein said 3-cyanopropanal is prepared in situ by the hydrolysis of an acetal selected from the group consisting of compounds having the formula:

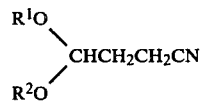

wherein R¹ and R² are independently lower alkyl, and mixtures thereof.

3. The process of claim 1 wherein a catalyst ratio of about from 0.05 to 1 g of copper-chromite catalyst is used per gram of said 3-cyanopropanal compound.

4. The process of claim 1 wherein said copper-chromite catalyst has been prereduced with hydrogen by contact with hydrogen in a liquid organic medium at temperatures in the range of about from 130 to 250° C. for about 30 to 180 minutes.

5. The process of claim 4 wherein said organic medium is selected from the group consisting of gamma-butyrolactone, tetrahydropyran, methanol, ethanol, tetrahydrofuran, and mixtures thereof.

6. The process of claim 1 wherein said reaction mixture comprises a solvent selected from the group consisting of water, inert organic solvents, and mixtures thereof.

7. The process of claim 5 wherein said solvent is selected from the group consisting of water, gamma-butyrolactone, tetrahydrofuran, methanol, ethanol, benzene, toluene, and mixtures thereof.

8. The process of claim 1 wherein said reducing agent was selected from the group consisting of alkanols, cycloalkanols and mixtures thereof.

9. The process of claim 8 wherein a catalyst ratio of about from 0.05 to 1 g of copper-chromite catalyst is used per gram of said 3-cyanopropanal.

10. The process of claim 2 wherein said copper-chromite catalyst is prereduced by contact with hydrogen in a liquid organic medium at temperatures in the range of about from 50 to 200° C.

11. The process of claim 8 wherein said organic medium is selected from the group consisting of water, gamma-butyrolactone, tetrahydrofuran, methanol, ethanol, benzene, toluene, and mixtures thereof.

12. The process of claim 8 wherein said reaction mixture comprises a solvent selected from the group consisting of water, inert organic solvents, and mixtures thereof.

13. The process of claim 12 wherein said solvent is selected from the group consisting of water, gamma-butyrolactone, tetrahydrofuran, methanol, ethanol, benzene, toluene, and mixtures thereof.

* * * * *